(12) United States Patent
Hsu et al.

(10) Patent No.: US 9,939,445 B1
(45) Date of Patent: Apr. 10, 2018

(54) DETECTION METHOD FOR CANCER CELL IN VITRO AND SYSTEM USING THE SAME

(71) Applicant: Chung Yuan Christian University, Taoyuan (TW)

(72) Inventors: Yih-Chih Hsu, Taoyuan (TW); Szetsen Lee, Taoyuan (TW)

(73) Assignee: CHUNG YUAN CHRISTIAN UNIVERSITY, Taoyuan (TW)

( * ) Notice: Subject to any disclaimer, the term of this patent is extended or adjusted under 35 U.S.C. 154(b) by 0 days.

(21) Appl. No.: 15/631,416

(22) Filed: Jun. 23, 2017

(30) Foreign Application Priority Data

Jan. 13, 2017 (TW) .............................. 106101309 A

(51) Int. Cl.

| | |
|---|---|
| *G01J 3/44* | (2006.01) |
| *G01N 33/58* | (2006.01) |
| *G01N 15/14* | (2006.01) |
| *G01N 33/50* | (2006.01) |
| *C12N 5/09* | (2010.01) |
| *C12Q 1/68* | (2018.01) |
| *C12N 5/00* | (2006.01) |
| *G01N 21/33* | (2006.01) |

(52) U.S. Cl.
CPC ......... *G01N 33/582* (2013.01); *C12N 5/0018* (2013.01); *C12N 5/0693* (2013.01); *C12Q 1/68* (2013.01); *G01N 15/147* (2013.01); *G01N 33/5005* (2013.01); *C12N 5/00* (2013.01); *C12N 2500/00* (2013.01); *G01N 21/33* (2013.01); *G01N 33/50* (2013.01)

(58) Field of Classification Search
CPC ... G01J 3/02; G01J 3/44; G01N 21/65; G01N 33/58; G01N 33/50; G01N 15/14; C12N 5/09; C12N 5/00; C12Q 1/68
See application file for complete search history.

(56) References Cited

U.S. PATENT DOCUMENTS

2010/0114514 A1* 5/2010 Wang ........................ G01J 3/02
702/82

* cited by examiner

*Primary Examiner* — Abdullahi Nur
(74) *Attorney, Agent, or Firm* — Muncy, Geissler, Olds & Lowe, P.C.

(57) ABSTRACT

A cancer cell detection system includes a sample holder, a laser light source, a light detector, and a determine module. The sample holder holds a cell measurement component having metal nanoparticles, and a cell sample is on the cell measurement component. The laser light source illuminates the cell sample. The light detector detects a surface enhanced Raman scattering signal of the cell sample. The determine module selectively determines if the cell sample includes a cancer cell according to a signal intensity of a valid signal in a first Raman peak and a signal intensity of a valid signal in a second Raman peak. The first Raman peak is the signal position of the ring breathing mode of adenine, and the second Raman peak is the signal position of the stretching mode of adenine.

20 Claims, 11 Drawing Sheets

DETECTION METHOD FOR CANCER CELL IN VITRO AND SYSTEM USING THE SAME

CROSS-REFERENCE TO RELATED APPLICATION

This non-provisional application claims priority under 35 U.S.C. § 119(a) to Patent Application No. 106101309 filed in Taiwan, R.O.C. on Jan. 13, 2017, the entire contents of which are hereby incorporated by reference.

BACKGROUND

Technical Field

The instant disclosure relates to detection techniques of cancer cells, in particular, to a detection method for cancer cell in vitro and system using the same.

Related Art

Cancer, also called malignant tumor, is a disease in which the cells of a creature are proliferating abnormally and the proliferating cells would further invade and attack other tissues or organs of the creature. The common cancers for male are the lung cancer, the prostate cancer, the colorectal cancer, and the stomach cancer; the common cancers for female are the breast cancer, the colorectal cancer, the lung cancer, and the cervical cancer; while the common cancers for child are the acute lymphoblastic leukemia and the brain cancer. Reasons leading to the cancers are complex and diverse. For example, genetic factors, obesity, smoking, drinking, lacking exercise, infection, radiation, dietary habits, and chronic inflammation may possibly cause the cells to be cancerated.

Because the cancer is not easy to cure, methods for detecting cancer are developed. However, the conventional methods cannot provide accurate and fast detection result. As a result, when it is confirmed that a patient have cancer, the golden time for cancer treatment is already gone, and the patient cannot be treated properly.

SUMMARY

Because conventional cancer detection methods still fail to provide fast and accurate cancer detection. Related personnel are devoted in developing a way for cancer cell detection for earlier treatment.

In one embodiment, a cancer cell detection system comprises a sample holder, a laser light source, a light detector, and a determine module. The sample holder is used to hold a cell measurement component. The cell measurement component has a plurality of metal nanoparticles, and a cell sample is located on the cell measurement component. The laser light source generates an incident light to illuminate the cell sample. The light detector detects a surface enhanced Raman scattering (SERS) signal of the cell sample. The determine module is coupled to the light detector. The determine module selectively determines if the cell sample comprises a cancer cell or if the cell sample is a normal cell sample according to a signal intensity of the valid signal in a first Raman peak and a signal intensity of a valid signal in a second Raman peak of the SERS signal of the cell sample. Wherein, the first Raman peak is a signal position of a ring breathing mode of adenine, and the second Raman peak is a signal position of a stretching mode of adenine.

In one embodiment, a detection method for cancer cell in vitro comprises utilizing a laser light source to illuminate a cell sample on a cell measurement component, wherein the cell measurement component comprises a plurality of metal nanoparticles; detecting a surface enhanced Raman scattering (SERS) signal of the cell sample; and selectively determining if the cell sample comprises a cancer cell or if the cell sample is a normal cell sample according to a signal intensity of a valid signal in a first Raman peak and a signal intensity of a valid signal in a second Raman peak of the SERS signal of the cell sample, wherein the first Raman peak is a signal position of a ring breathing mode of adenine, and the second Raman peak is a signal position of a stretching mode of adenine.

As above, according to the system and the method of the instant disclosure, by analyzing the ratio between certain vibration modes of the DNA of the cell sample, the cell sample can be determined to be a cancer cell sample or a normal cell sample in a fast and accurate manner.

BRIEF DESCRIPTION OF THE DRAWINGS

The disclosure will become more fully understood from the detailed description given herein below for illustration only, and thus not limitative of the disclosure, wherein:

FIGS. 4A to 4E illustrate surface enhanced Raman scattering (SERS) spectra of oral cancer cells and fibroblasts measured with different gold nanoparticles, wherein FIG. 4A illustrates a SERS spectrum of oral cancer cells and fibroblasts measured with gold nanoparticles manufactured by sodium citrate reduction, FIG. 4B illustrates a SERS spectrum of oral cancer cells and fibroblasts measured with gold nanoparticles manufactured by sodium borohydride reduction, FIG. 4C illustrates a SERS spectrum of oral cancer cells and fibroblasts measured with triangular gold nanoparticles manufactured by ethylene glycol, FIG. 4D illustrates a SERS spectrum of oral cancer cells and fibroblasts measured with large polyhedron gold nanoparticles manufactured by ethylene glycol, and FIG. 4E illustrates a SERS spectrum of oral cancer cells and fibroblasts measured with small polyhedron gold nanoparticles manufactured by ethylene glycol;

DETAILED DESCRIPTION

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values, and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the instant disclosure and attaching claims are approximations that can vary as desired. At the very least, each numerical parameter should at least be construed in light of the number of reported significant digits and by applying ordinary rounding techniques.

Unless defined otherwise, all technical and scientific terms used herein have the same meaning as commonly understood by one of the ordinary skill in the art to which this invention belongs. The singular forms "a", "and", and "the" are used herein to include plural referents unless the context clearly dictates otherwise; conversely, terms with the plural forms used herein include singular referents.

Figure 1:
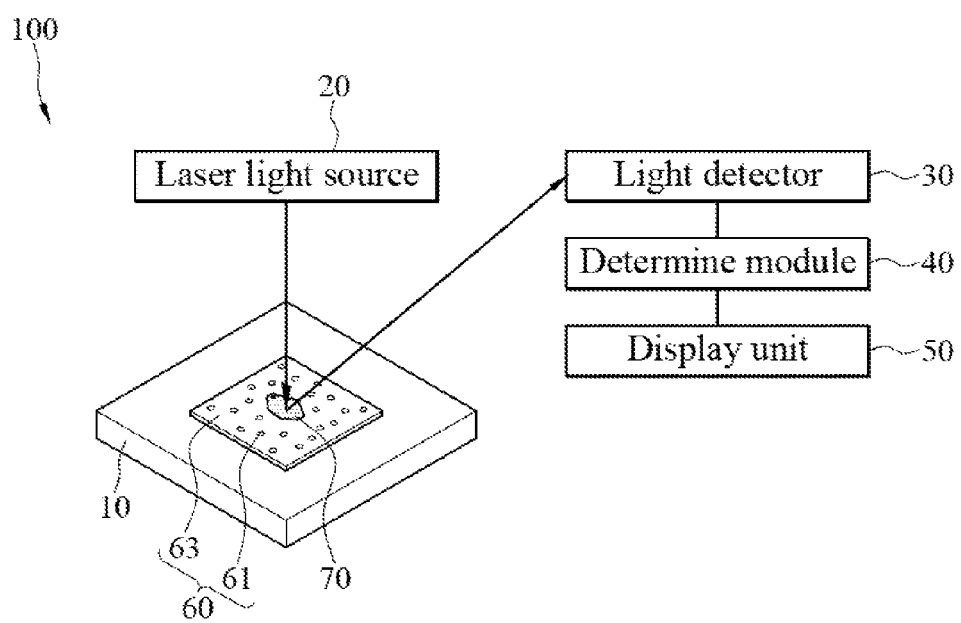
FIG. 1 illustrates a schematic view of a cancer cell detection system of an exemplary embodiment of the instant disclosure.

FIG. 1 illustrates a schematic view of a cancer cell detection system of an exemplary embodiment of the instant disclosure. Please refer to FIG. 1. In one embodiment, the cancer cell detection system 100 is used along with a cell measurement component 60. The cell measurement component 60 comprises a plurality of metal nanoparticles 61, and a cell sample 70 is on the cell measurement component 60. For example, the cell sample 70 may be, but not limited to, a squamous epithelial cell sample or an esophageal cell sample. In some embodiments, prior to the detection, the cell sample 70 is applied and cultivated on the cell measurement component 60 in advance.

In one embodiment, as shown in FIG. 1, the cell measurement component 60 may further comprise a base plate 63, and the metal nanoparticles 61 are distributed over the base plate 63. In this embodiment, the cell sample 70 is applied on a surface of the base plate 63 having the metal nanoparticles 61. In some embodiments, the base plate 63 may be a silicon substrate. It understood that, in the foregoing embodiments, the base plate 63 is a dried substrate, but the cell measurement component 60 may be in a form of glue substrate or a semiarid substrate. In other words, the solution containing the metal nanoparticles 61 may be applied on the base plate 63 in a form of droplet, and then the cell sample 70 is applied in the droplet.

In some embodiments, the metal nanoparticles 61 are manufactured in solution followed by being applied to the base plate 63. In some other embodiments, the metal nanoparticles 61 may be deposited on the base plate 63 by semiconductor manufacturing processes.

In some embodiments, the metal nanoparticles 61 may be gold nanoparticles. In one embodiment, the gold nanoparticles may be, but not limited to, manufactured by the reaction of sodium citrate, sodium borohydride, cetyltrimethylammonium bromide (CTAB), or polyvinylpyrrolidone (PVP) plus a precursor (e.g., chloroauric acid). In another embodiment, the gold nanoparticles are manufactured by sodium borohydride reduction to prevent organic substances being left on the gold nanoparticles. Accordingly, the spectrum obtained with the $NaBH_4$-reduced gold nanoparticles has less interference sources.

As shown in FIG. 1, the cancer cell detection system 100 comprises a sample holder 10, a laser light source 20, a light detector 30, and a determine module 40. The determine module 40 is coupled to the light detector 30.

The sample holder 10 is used to hold the cell measurement component 60. In one embodiment, the sample holder 10 may be a plate, and the cell measurement component 60 is on the surface of the plate. In another embodiment, the sample holder 10 may have several limiting portions (e.g., two L shaped rods or four posts) and a base, and the cell measurement component 60 is assembled and limited between the limiting portions and the base.

Figure 2:
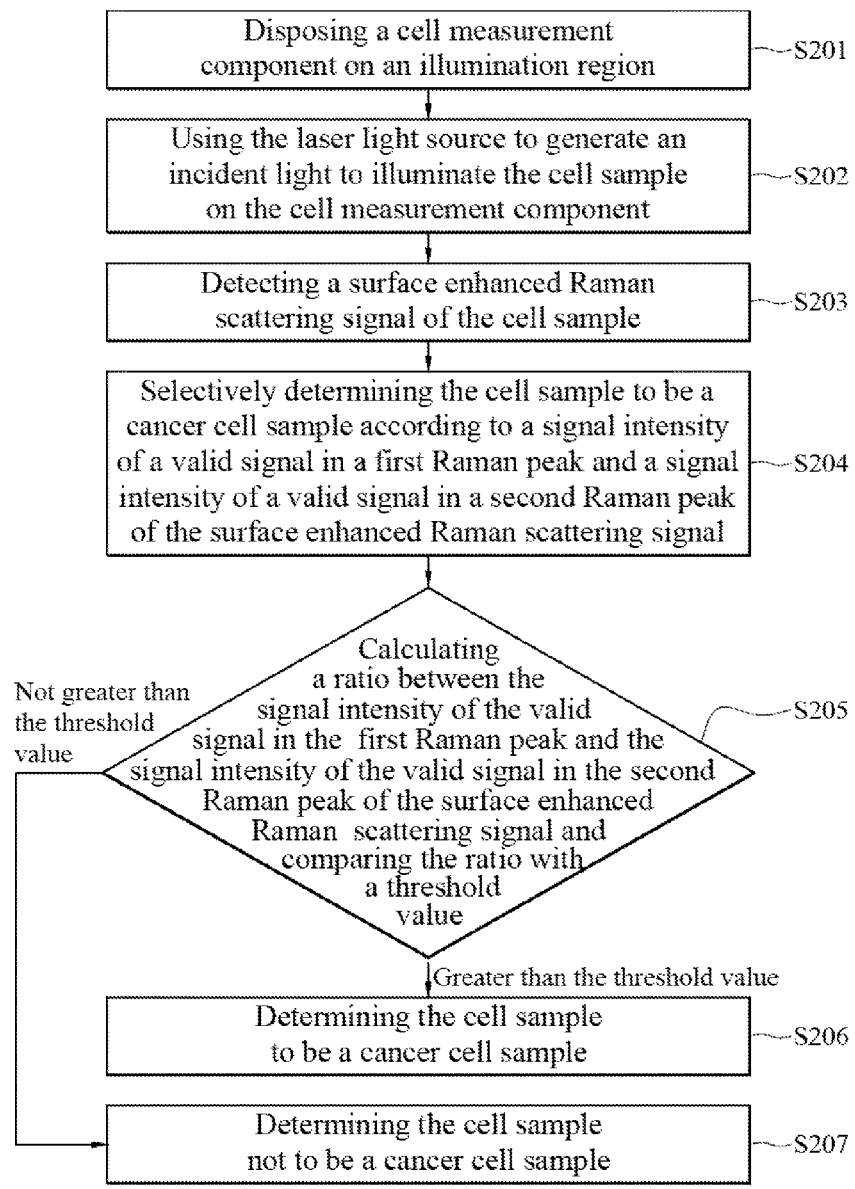
FIG. 2 illustrates a flowchart of a detection method for cancer cell in vitro of an exemplary embodiment of the instant disclosure.

FIG. 2 illustrates a flowchart of a detection method for cancer cell in vitro of an exemplary embodiment of the instant disclosure. Please refer to FIGS. 1 and 2. In the detection, the sample holder 10 may move the cell measurement component 60 held on the sample holder 10 to an excitation region; namely, the cell measurement component 60 is disposed on an illumination region (step S201). The laser light source 20 is used to generate an incident light to the illumination region to illuminate the cell sample 70 in the illumination region (the cell sample 70 is on the cell measurement component 60) (step S202). In some embodiments, the wavelength of the laser light source 20 may be in one wavelength region of the vacuum ultraviolet, the ultra violet, the visible, the near infrared, the infrared, and the far infrared. In one embodiment, the laser light source 20 may emit a visible light, so that when the laser light source 20 illuminates on the cell sample 70, the fluorescence interferences caused by the illumination can be reduced. Furthermore, the wavelength of the laser light source 20 may be, but not limited to, 632.8 nm to correspond to the absorption wavelength of the gold nanoparticles.

After the illumination, the light detector 30 then detects a surface enhanced Raman scattering (SERS) signal of the cell sample 70 (step S203). After the incident light illuminates on the cell sample 70, the incident light may be reflected, scattered or may undergo photochemical reaction with the illuminated object. When the wavelength of a scattered light is greater than the wavelength of the incident light, it is called Raman scattering. Furthermore, because the incident light also illuminates on the metal nanoparticles 61, the metal nanoparticles 61 can provide strong local electromagnetic field for the cell sample 70 when the wavelength of the incident light is proper to resonate with the plasmons on the surface of the metal nanoparticles 61, thereby implementing the surface enhanced Raman scattering.

In some embodiments, the light detector 30 may comprise a spectrophotometer and a charge-coupled device (CCD). Scattered lights having different wavelengths from the cell sample 70 are dispersed by the spectrophotometer and entering into different positions of the charge-coupled device. Hence, the charge-coupled device continuously records the intensities of the light having different wavelengths at the same time to obtain a Raman spectrum. It is understood that, the Raman spectrum obtained from the light detector 30 may have not only from the SERS signals of the cell sample 70 but may also from Raman signals or SERS signals contributed by a small amount of organic and/or inorganic compounds left on the metal nanoparticles 61 (which may be, but not limited to, unreacted reductant or capping agent). Furthermore, the light detector 30 may further comprise a notch filter. The notch filter can eliminate most of the Rayleigh scattering signals, so that a spectrum with less interferences of background incident light can be obtained.

The determine module 40 selectively determines if the cell sample 70 comprises a cancer cell (for the sake of convenience, the cell sample comprising a cancer cell is called a cancer cell sample) according to a signal intensity of a valid signal in a first Raman peak and a signal intensity of a valid signal in a second Raman peak of the surface enhanced Raman scattering signal (step S204). In some embodiments, the determine module 40 may calculate a ratio between the signal intensity of the valid signal in the first Raman peak and the signal intensity of the valid signal in the second Raman peak of the surface enhanced Raman scattering signal (for the sake of convenience, called the ratio) and compare the ratio with a threshold value (step S205). When the ratio is greater than the threshold value, the determine module 40 determines the cell sample to be a cancer cell sample (step S206). Conversely, when the ratio is not greater than the threshold value, the determine module 40 determines the cell sample not to be a cancer cell sample (step S207).

Wherein, the first Raman peak is a signal position of a ring breathing mode (RBM) of adenine, and the second Raman peak is a signal position of a stretching mode of Adenine. In one embodiment, the stretching mode of adenine comprises a carbon-carbon stretching mode and a carbon-nitrogen stretching mode. For example, when the wavelength of the incident light generated by the laser light source is 632.8 nm, the first Raman peak is at about 735 $cm^{-1}$, and the second Raman peak is at about 1342 $cm^{-1}$.

In one embodiment, the cancer cell detection system 100 may further comprise a display unit 50 electrically connected to the determine module 40. The display unit 50 is used to display the SERS signal of the cell sample 70 and/or the determination result of the cell sample 70. In one embodiment, the display unit 50 may directly display the valid signal in the first Raman peak and the valid signal in the second Raman peak of the surface enhanced Raman scattering signal of the cell sample 70 in a form of waveform. Or, the display unit 50 may directly display the signal intensity of the valid signal in the first Raman peak and the signal intensity of the valid signal in the second Raman peak of the surface enhanced Raman scattering signal of the cell sample 70 in a form of magnitude. Alternatively, the display unit 50 may display a waveform of a range containing the signal positions of the first Raman peak and the second Raman peak of the SERS signal of the cell sample 70. That is, the display module 50 may display the SERS spectrum of the cell sample 70 in the range containing the first Raman peak and the second Raman peak. For example, in the case that the first Raman peak is at about 735 $cm^{-1}$ and the second Raman peak is at about 1342 $cm^{-1}$, the range may be from 400 $cm^{-1}$ to 4000 $cm^{-1}$. In some embodiments, the display unit 50 may just display the determination result, so that an operator can know that if the cell sample 70 is a cancer cell sample instantly.

As shown in the subsequent experimental sections, when the cell sample 70 is a normal cell sample, the ratio is less than or greater than a threshold value; conversely, when the cell sample 70 is a cancer cell sample, the ratio is greater than the threshold value. It is understood that, the magnitude of the threshold value may be different when the type of the cancer is different. Accordingly, the system and the method according to embodiments of the instant disclosure are capable of performing a rapid and accurate determination for cancer cell sample.

Furthermore, in one embodiment, the threshold value may be a ratio between a signal intensity of a valid signal in the first Raman peak and a signal intensity of a valid signal in the second Raman peak of a surface enhanced Raman scattering signal of a normal cell sample. The threshold value is a basis for determining if the cell sample 70 is a cancer cell sample. In one embodiment, the signal intensity of the valid signal is the peak value of the valid signal, namely, a relative intensity value at the peak. In other words, the determine module 40 determines if the ratio between the peak value of the valid signal in the first Raman peak and the peak value of the valid signal in the second Raman peak of the SERS signal of the cell sample 70 is greater than the threshold value, if yes, the determine module 40 determines the cell sample 70 to be a cancer cell sample. In another embodiment, the signal intensity of the valid signal may be a value of area integration of the valid signal. In other words, the determine module 40 determines if the ratio between a value of area integration of the valid signal in the first Raman peak and a value of area integration of the valid signal in the second Raman peak of the SERS signal of the cell sample 70 is greater than the threshold value, if yes, the determine module 40 determines the cell sample 70 to be a cancer cell sample. In yet another embodiment, the determine module 40 firstly determines if the ratio between the peak value of the valid signal in the first Raman peak and the peak value of the valid signal in the second Raman peak of the SERS signal of the cell sample 70 is greater than the threshold value, if yes, the determine module 40 then determines if the ratio between a value of area integration of the valid signal in the first Raman peak and a value of area integration of the valid signal in the second Raman peak of the SERS signal of the cell sample 70 is greater than the threshold value, if yes, the determine module 40 determines the cell sample 70 to be a cancer cell sample. Accordingly, the multiple determination steps can reduce the possibility of misdetermination. It is understood that, the calculation of the value of the area integration may be achieved by statistics software which is built in the determine module 40 or additionally installed to the determine module 40.

As above, with the system and the method according to embodiments of the instant disclosure, the cancer cell sample can be determined rapidly and accurately, by comparing the ratio of the signal intensities of certain vibration modes of deoxyribonucleic acid (DNA) of the cell sample. Specifically, the system and the method according to some embodiments of the instant disclosure can be used in determining oral or esophageal cancers, but it is understood that, the system and the method can also be used in determining other cancers.

The following Examples are provided to elucidate certain aspects of the instant disclosure. These Examples are in no way to be considered to limit the scope of the invention in any manner.

1. Preparation of Gold Nanoparticles 1.1 Preparation of Gold Nanoparticles Manufactured by Sodium Borohydride Reduction Firstly, chloroauric acid is added to deionized water to prepare a $5 \times 10^{-4}$ M chloroauric acid solution. On the other hand, sodium borohydride is added to deionized water to prepare a $10^{-2}$ M sodium borohydride solution and the solution is stored in ice bath. Next, the ice-bathed sodium borohydride solution is added to the chloroauric acid solution in droplet (each about 60 micrometers) with the chloroauric acid solution being continuously stirred in the addition. After the addition, the mixture is further stirred for an hour to allow the chemicals to react with each other thoroughly, thereby the gold nanoparticle solution can be prepared (symbolized by nanoAu(NaBH$_4$)).

1.2 Preparation of Gold Nanoparticles Manufactured by Sodium Citrate Reduction

Firstly, chloroauric acid is added to deionized water to prepare a 10$^{-3}$ M chloroauric acid solution. Then, chloroauric acid solution is heated to boil, followed by slowly adding a sodium citrate solution having a weight percentage of 1% as the reductant. After the mixture is continuously boiling for 15 minutes, a gold nanoparticles crude solution is prepared. Next, the crude solution is cooled and centrifuged for 5 minutes (13000 rpm). After the centrifugation, the supernatant which accounts for 90% of the mixture is removed and the gold nanoparticle solution at the lower part of the mixture which accounts for 10% of the mixture is retained (symbolized by nanoAu(citrate)).

1.3 Preparation of Gold Nanoparticles Manufactured by Ethylene Glycol 1.3.1 Triangular Gold Nanoparticles Firstly, polyvinylpyrrolidone (PVP) is dissolved in ethylene glycol. Next, a 0.5 M chloroauric acid solution is added to the PVP-dissolved solution. The mixture is then ultrasonicated for 10 minutes to obtain a pale yellow clear solution. Under 195 Celsius degrees and without stirring (0 rpm), the pale yellow clear solution is reacted for 5 minutes. Then, a 10$^{-3}$ M silver nitrate aqueous solution is added to the yellow solution to react for one hour to form gold nanoparticles in triangular shape (symbolized by nanoAu(PVP)). Next, the gold nanoparticle solution is centrifuged for 20 minutes (6000 rpm) to remove the supernatant and to collect the precipitates (i.e., the triangular gold nanoparticles). Then, the precipitates are rinsed with 95% alcohol and ultrasonicated for 10 minutes. The above purification step is repeated ten times. Finally, the triangular gold nanoparticles are stored in 95% alcohol.

1.3.2 Polyhedron Gold Nanoparticles

Firstly, cetyltrimethylammonium bromide (CTAB) is dissolved in ethylene Glycol. Next, a 0.5 M chloroauric acid solution is added to the PVP-dissolved solution and mixed thoroughly. Then, under 195 Celsius degrees and with stirring, the mixture is reacted for 50 minutes to form polyhedron gold nanoparticles. Next, the gold nanoparticle solution is centrifuged for 20 minutes (6000 rpm) to remove the supernatant and to collect the precipitates (i.e., the polyhedron gold nanoparticles). Then, the precipitates are rinsed with 95% alcohol and ultrasonicated for 10 minutes. The above purification step is repeated for ten times. Finally, the polyhedron gold nanoparticles are stored in 95% alcohol.

Wherein, in forming polyhedron gold nanoparticles with larger sizes, the stirring speed can be adjust to 100 rpm for 50 minutes to form polyhedron gold nanoparticles with a size about 1 μm (symbolized by nanoAu(CTAB)A). Conversely, in forming polyhedron gold nanoparticles with larger sizes, the stirring speed can be adjust to 500 rpm for 50 minutes to form polyhedron gold nanoparticles with a size about 100 nanometers (symbolized by nanoAu(CTAB)B).

As shown in Table 1, the size of nanoAu(citrate) is about 30 nm, the size of nanoAu(NaBH$_4$) is about 25 nm, the size of nanoAu(PVP) is about 80 nm, the size of nanoAu(CTAB)A is about 1 μm, and the size of nanoAu(CTAB)B is about 100 nm.

TABLE 1

| Gold nanoparticles | Size (nm) | Shape |
|---|---|---|
| nanoAu(NaBH$_4$) | 25 ± 5 | Spherical |
| nanoAu(citrate) | 29.13 ± 3.92 | Spherical |
| nanoAu(PVP) | 80.15 ± 18.27 | Triangular |
| nanoAu(CTAB)A | 971.25 ± 158.12 | Polyhedron |
| nanoAu(CTAB)B | 93.28 ± 21.71 | Polyhedron |

2. Preparation of Cell Measurement Component

The silicon chip is cut to have a proper size, and the silicon chip is then placed in deionized water to ultrasonicate for 30 minutes for cleaning the surface of the chip. Accordingly, a substrate is obtained. The prepared gold nanoparticles according to the foregoing embodiments are added on the substrate in droplet (each about 50 microliters). Then, the substrate is dried in vacuum box. The foregoing coating and drying steps are repeated four times to allow the gold nanoparticles sufficiently covering the surface of the substrate.

3. Cell Culture 3.1 Oral Cancer Cell (SAS and SCC4 Cells)

The SAS cell line is established by a tongue cancer specimen, the SAS cell line is a poorly differentiated oral squamous-cell carcinoma and is the tongue cancer cell from a Taiwanese. The SCC4 cell line is the oral squamous-cell carcinoma from a 55-year-old male and purchased from Food Industry Research and Development Institute (labeled with BCRC-SCC4-60142). The culture condition of the cancer cells is 37 Celsius degrees, 5% $CO_2$ atmosphere, Dulbecco's modified eagle media/F12 (DMEM/F12) culture medium, and in the incubator. The way for preparing the culture medium is, dissolving the DEMEM/F12 powder (containing L-glutamine and 4-(2-hydroxyethyl)-1-piperazineethanesulfonic acid (HEPES)), sodium carbonate ($Na_2CO_3$), and hydrocortisone in deionized water to prepare a 1-L culture medium having pH value of 7.2 to 7.4. Next, fetal bovine serum (FBS) is added to the culture medium and the FBS-added culture medium is filtered by a filter membrane having a pore diameter of 0.22 micrometers and stored in a serum bottle.

3.2 Normal Human Foreskin Fibroblast Cell (HFF)

The HFF cell line is the normal human foreskin fibroblast of a 40-year-old Taiwanese. The culture condition of the cells is 37 Celsius degrees, 5% $CO_2$ atmosphere, DMEM/F12 culture medium, and in the incubator. The way for preparing the culture medium is, dissolving the DEMEM/F12 powder (containing L-glutamine and L-glucose) and sodium carbonate ($Na_2CO_3$) in deionized water to prepare a 1-L culture medium. Then, the pH value of the culture medium is adjusted to 7.2 to 7.4 by hydrochloric acid or sodium hydroxide. Next, fetal bovine serum (FBS) is added to the culture medium and the FBS-added culture medium is filtered by a filter membrane having a pore diameter of 0.22 micrometers and stored in a serum bottle.

3.3 Esophageal Cancer Cells (CE48T and CE81T Cells)

The CE48T cell line is the epithelial cancer cells of a 58-year old Taiwanese having esophageal cancer, and the CE81T cell line is the epithelial cancer cells of a 57-year old Taiwanese having esophageal cancer. The culture condition of the cancer cells is 37 Celsius degrees, 5% $CO_2$ atmosphere, Roswell Park Memorial Institute-1640 (RPMI-1640) culture medium, and in the incubator. The way for preparing the culture medium for the esophageal cancer cell lines is, preparing a 1-L RPMI-1640 culture medium. Then, fetal bovine serum (FBS) is added to the culture medium. Next, L-glutamine is added to the FBS-added culture medium, and the culture medium is filtered by a filter membrane having a pore diameter of 0.22 micrometers and stored in a serum bottle.

3.4 Normal Esophageal Cell (Het-1A)

The Het-1A cell line is the epithelial cell of a 25-year old Taiwanese. The culture condition of the cells is 37 Celsius degrees, 5% $CO_2$ atmosphere, Bronchial epithelial cell growth medium (BEGM) culture medium, with the cell-culture dish, and in the incubator. The way for preparing the culture medium for the esophageal cell line is, preparing a 500-ml BEGM culture medium with 9 frozen tubes. Then, the culture medium is added to the frozen tubes with the micropipette.

Subculture of Cell Lines

When the cells grow to have a size of 70% of that of the cell-culture dish, the cells are to be subcultured. The subculture step is:

A. removing old culture medium in the cell-culture dish, and rinsing the cells twice with phosphate slat buffer solution.

B. adding trypsin-ethylenediaminetetraacetic acid (trypsin-EDTA) to the cell-culture dish and placing the cell-culture dish in the incubator for 10 minutes under 37 Celsius degrees.

C. checking until substantially 90% of the cells are migrating from the dish to trypsin-EDTA, i.e., the cells are changed from a state of closely attaching onto the dish to a state of suspending in trypsin-EDTA. The checking may be accomplished with microscope.

D. adding the culture medium to the cell-culture dish to terminate the function of trypsin-EDTA.

E. collecting the solution (i.e., the cell solution) and storing one-fourth of the cell solution back to the cell-culture dish or a new dish, and filling the dish with the culture medium.

F. in subculturing the esophageal cell (both the cancer cells and the normal cells), the cell solution should be centrifuged (1000 rpm, 3 minutes). Hence, the cells are precipitated to the bottom of the centrifuged tube, so that the culture medium containing trypsin-EDTA can be removed. After adding the new culture medium to the centrifuged tube, the tube is slightly shaken to mix the cells and the medium, thereby allowing the cells suspending in the culture medium. Next, the cells may be cultured to the cell-culture dish or a new dish.

G. culturing the cells in the incubator under a condition of 37 Celsius degrees and 5% $CO_2$ atmosphere.

5. Preparation for Cell Sample for SERS Spectrum Measurement

Firstly, counting the collected subculture cell solution, and the number of the cells in each cell sample is about $10^8$. Next, the cell solution is centrifuged for 3 minutes (1000 rpm) to remove all of the supernatant. Then, 50 μl deionized water is added to and mixed with the cell solution by micropipette. And, 50 μl cell solution is added on the substrate in droplet and dried in the vacuum dry box for one hour.

6. Measurement of SERS Spectrum

In the experiment, the wavelength of the laser light source is 632.8 nm. Prior to the sample measurement, the instrument is calibrated by a silicon chip to check the Raman scattering signal of the silicon chip at 520.5 $cm^{-1}$. In the experiment, the slit width is 0.01 mm, the exposure time of the light detector is 1 to 20 seconds, and the scanning range of the spectrum is 400 to 4000 $cm^{-1}$ (the scanning range is the wavenumber difference between the scattered light and the incident light, i.e., the Raman shift).

Figure 3:
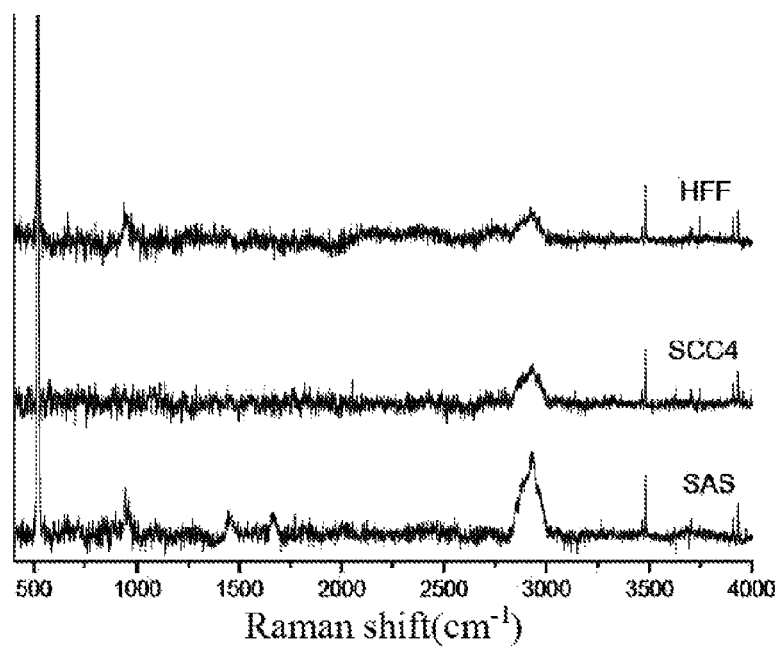
FIG. 3 illustrates a normal Raman spectrum of oral cancer cells (SAS and SCC4 cells) and fibroblast cells (HFF)
Figure 4A:
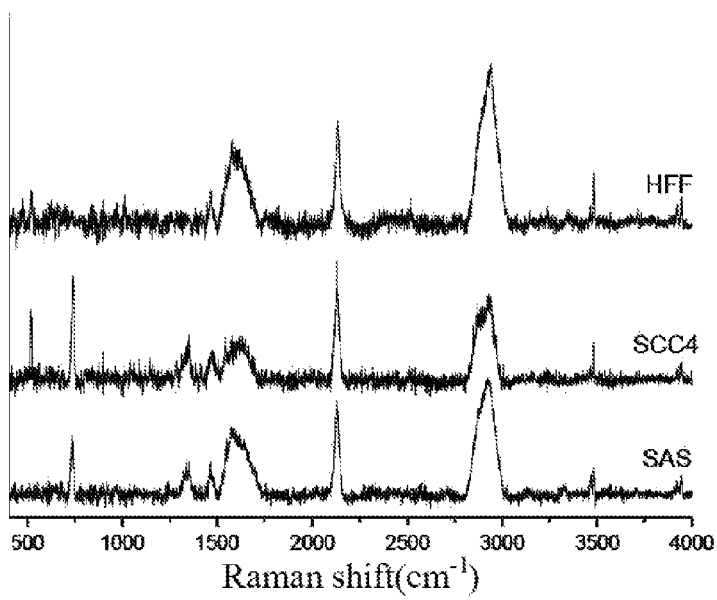
Figure 4B:
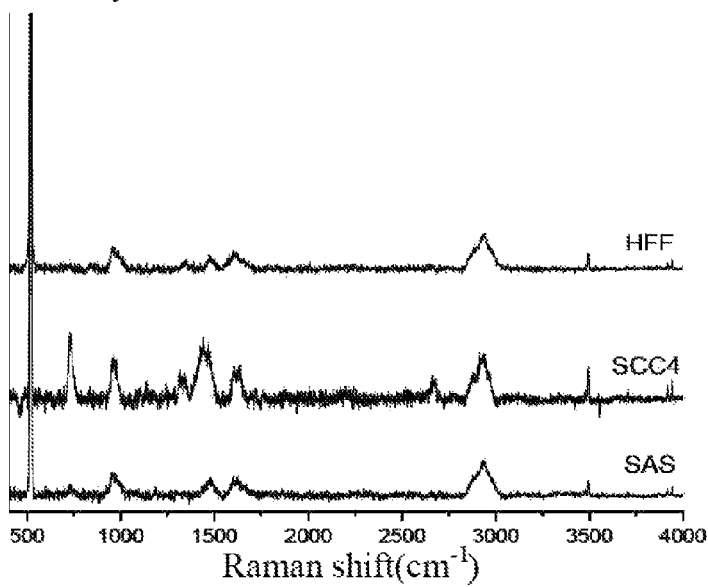
Figure 4C:
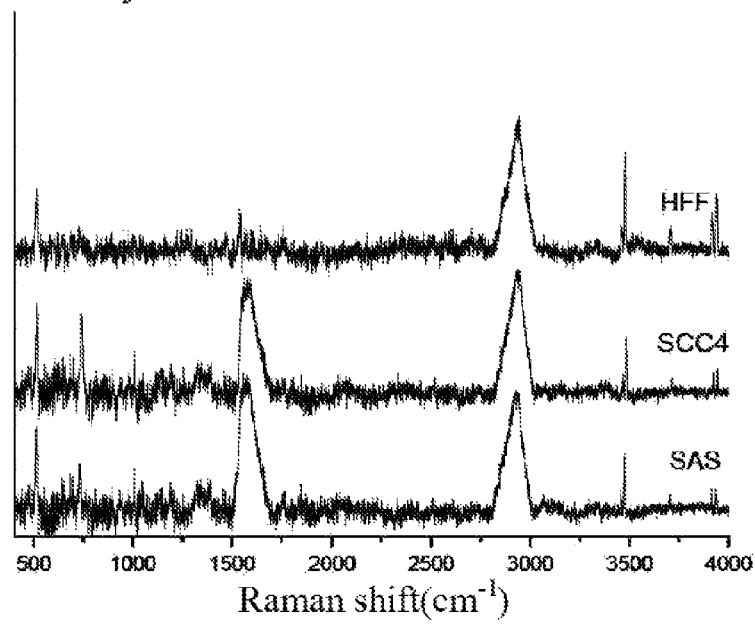
Figure 4D:
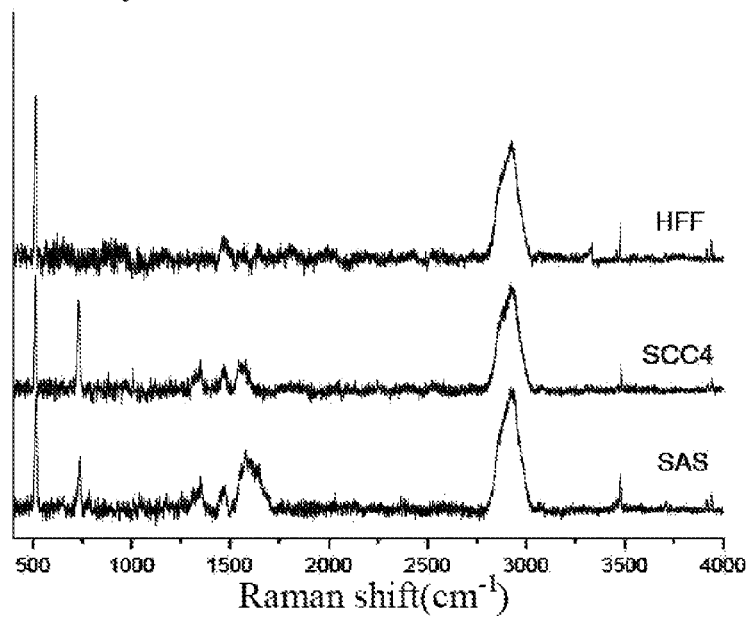
Figure 4E:
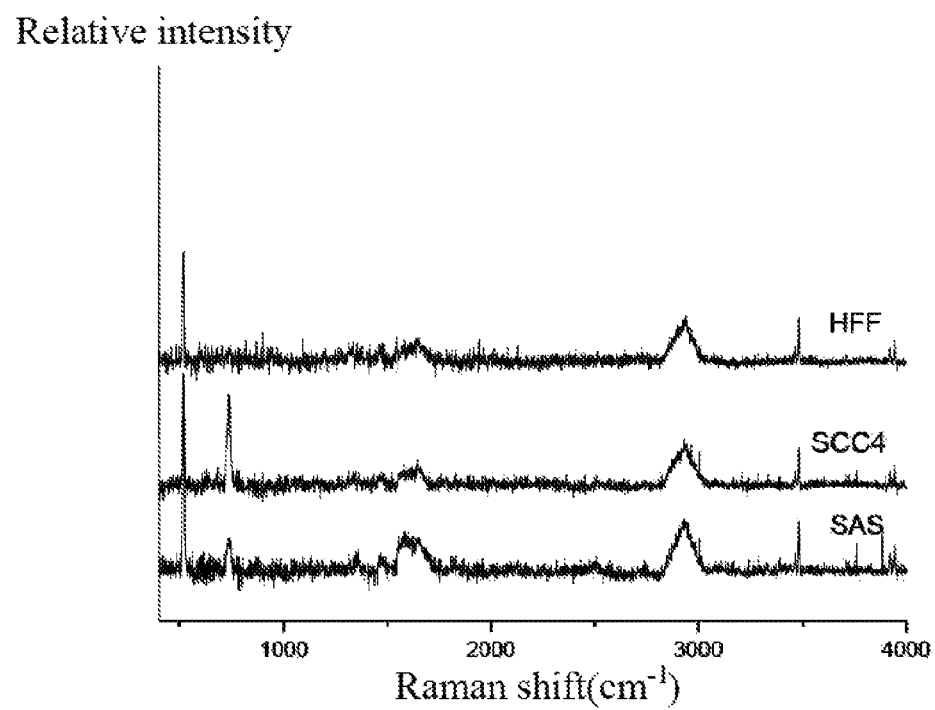
Figure 5A:
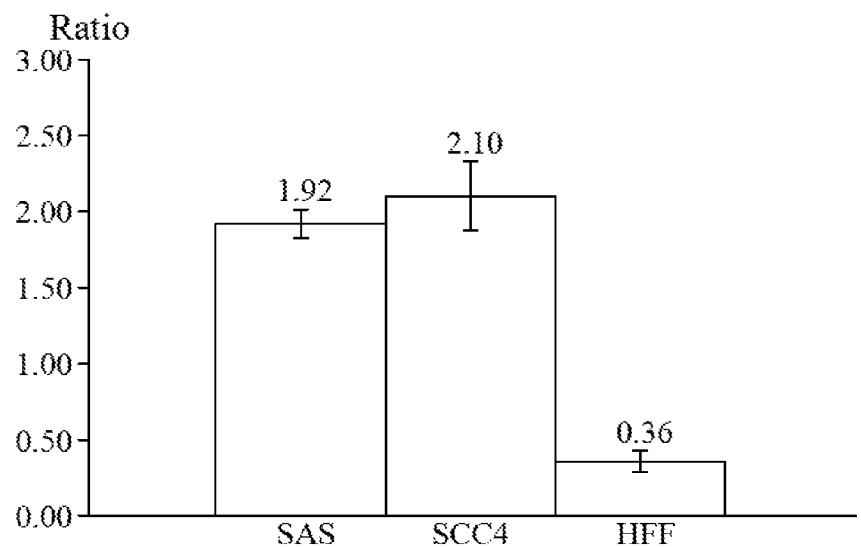
FIGS. 5A to 5E illustrate bar graphs of signal intensities of valid signals in a first Raman peak and a second Raman peak of the spectra in FIGS. 4A to 4E fitted by Gaussian function.
Figure 5B:
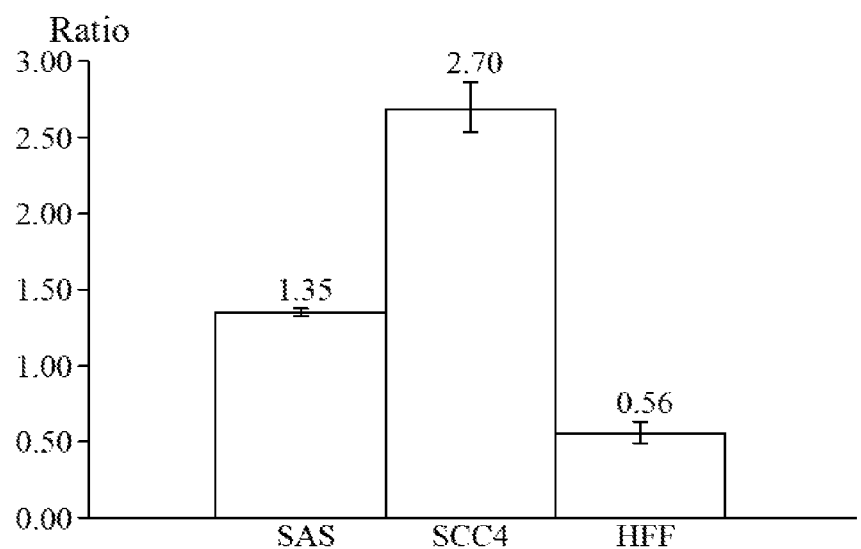
Figure 5C:
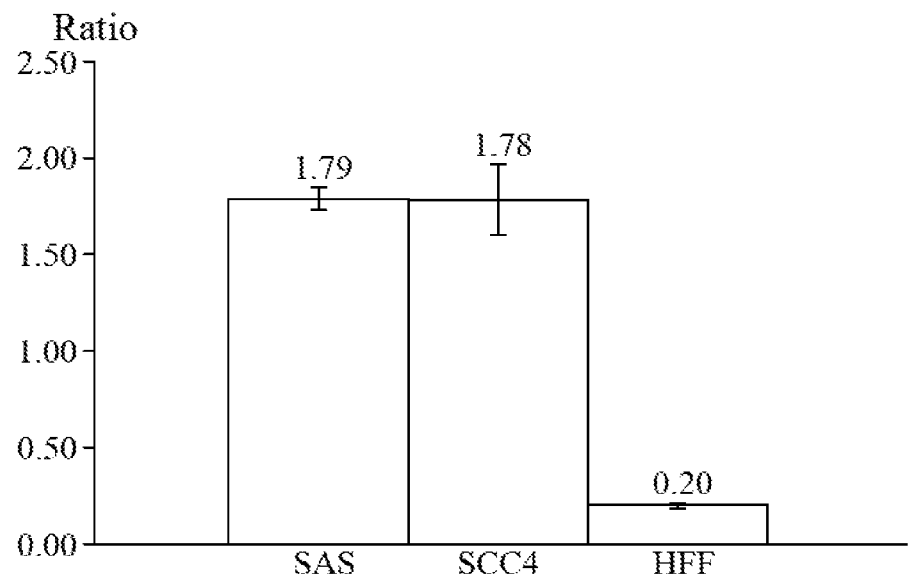
Figure 5D:
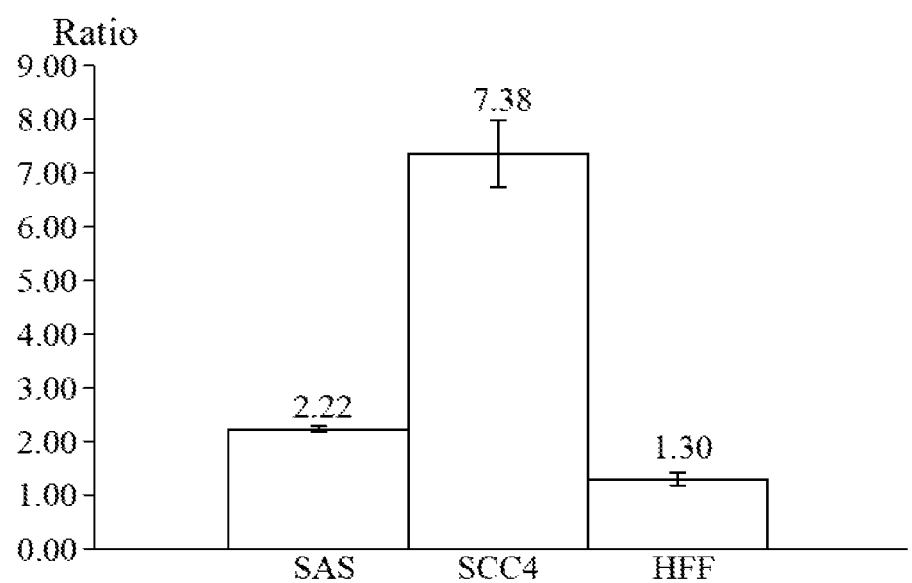
Figure 5E:
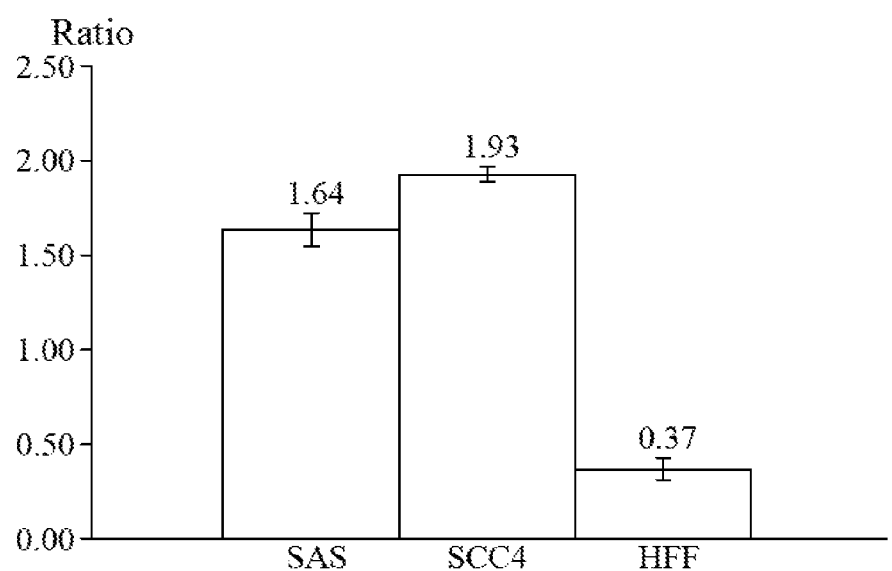

7. Analysis for Normal Raman and SERS Spectra of Oral Cancer Cells and Fibroblast Cells The spectrum measurement of oral cancer cells and fibroblast cells are provided, as shown in FIG. 3 and FIGS. 4A to 4E. It is understood that, the normal Raman signals (or the SERS signals) of the cell may come from nucleic acid, protein, lipid, and the metabolites, and among these, nucleic acid has apparent signals. FIG. 3 illustrates a normal Raman spectrum of oral cancer cells (SAS and SCC4 cells) and fibroblast cells (HFF), showing that the Raman signals of the cells are quite weak. FIGS. 4A to 4E illustrate surface enhanced Raman scattering (SERS) spectra of oral cancer cells and fibroblasts measured with different gold nanoparticles. Taking FIG. 4A as an example, when the cell is measured with gold nanoparticles manufactured by sodium citrate reduction and excited by the 632.8 nm laser, major SERS peaks are respectively at 735 $cm^{-1}$ (hereinafter called first Raman peak), 1342 $cm^{-1}$ (hereinafter called second Raman peak), 1450 $cm^{-1}$, and 1575 $cm^{-1}$. The SERS signal at the first Raman peak is apparent for the oral cancer cells (SAS and SCC4 cells) but respectively weaker for fibroblast cells (HFF cells). In the case of using a laser light having a wavelength of 632.8 nm, the first Raman peak is the signal position of the ring breathing mode of adenine, and the second Raman Peak is the signal position of the stretching mode of adenine. It is understood that, the signal intensity of the valid signal in the second Raman peak are not only contributed by the stretching mode of adenine. In fact, besides adenine, other nitrogenous bases in nucleic acid (i.e., guanine (G), thymine (T), and cytosine (C)) may contribute signal to the second Raman position. Furthermore, after comparing the SERS spectra of the cells with the normal Raman spectrum of adenine (as indicated in Table 2 and Table 3), most of the SERS signals of the cell sample come from the adenine, and the reason may be: (1) The ring breathing mode of adenine is most apparent among other vibration modes of nitrogenous bases; (2) Adenine may have ATP, ADP for storing energy, energy metabolite such as NADH and FAD, nucleic acid, and mitochondria DNA. As compared to a normal cell, a cancer cell needs more energy (i.e., more ATP and ADP), more metabolites (more NADH), and more DNA damages. Therefore, the SERS signal of adenine for oral cancer cells and that for normal fibroblast cells are different; and (3) Adenine and adenine adducts have similar Raman spectra.

TABLE 2

| (incident light: 632.8 nm laser light) | |
|---|---|
| Signal position | source |
| 735 $cm^{-1}$ | Adenine adducts (nucleic acid) |
| 1342 $cm^{-1}$ | Adenine adducts (nucleic acid) |
| 1450 $cm^{-1}$ | Lipid, nucleic acid, protein |
| 1575-1665 $cm^{-1}$ | Nucleic acid, protein |

TABLE 3

| (incident light: 632.8 nm laser light) | |
|---|---|
| Signal position | Vibration mode |
| 735 $cm^{-1}$ | Ring-breathing mode |
| 1341 $cm^{-1}$ | C-C stretching mode, C-N stretching mode |
| 1442 $cm^{-1}$ | C-C stretching mode, C-N stretching mode, C-H bending mode, N-H bending mode |
| 1605 $cm^{-1}$ | C-C stretching mode, C-N stretching mode, N-H bending mode, H-N-H scissoring mode |

8. Analysis and Comparison for the Curve Fitting of SERS Spectra of Oral Cancer Cells and Fibroblast Cells In order to realize the difference between the SERS spectra of the oral cancer cells and that of the normal cells at the first Raman peak (735 cm$^{-1}$) and the second Raman peak (1342 cm$^{-1}$), the signal intensities of the valid signals of Raman spectra obtained with different substrates at the first Raman peak and the second Raman peak are used for curve fitting by Gaussian function, and presented in a form of ratio. The experiments are repeated three times, and the averaged value is provided in FIGS. 5A to 5E.

As shown, the ratio between the signal intensity of the valid signal in the first Raman peak and the signal intensity of the valid signal in the second Raman peak of the SAS cells and that between the SCC4 cells are both greater than the ratio between the signal intensity of the valid signal in the first Raman peak and the signal intensity of the valid signal in the second Raman peak of the HFF cells (i.e., the normal cells).

Figure 6:
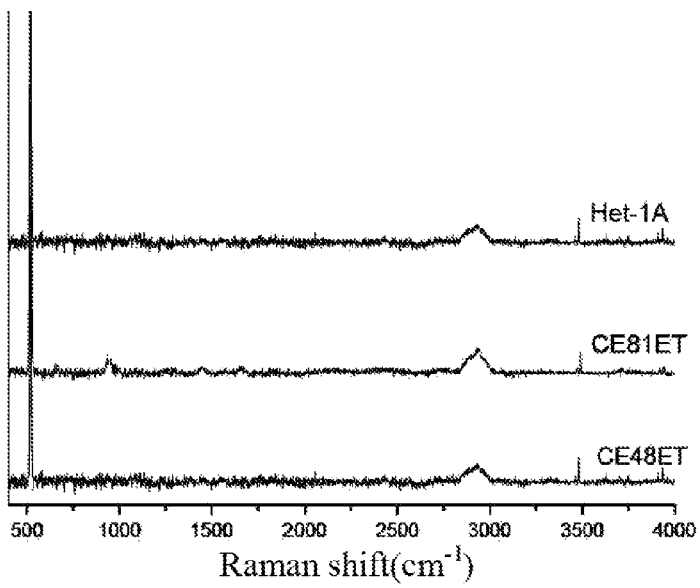
FIG. 6 illustrates a normal Raman spectrum of esophageal cancer cells (CE48T and CE81T cells) and normal esophageal cancer cells.
Figure 7:
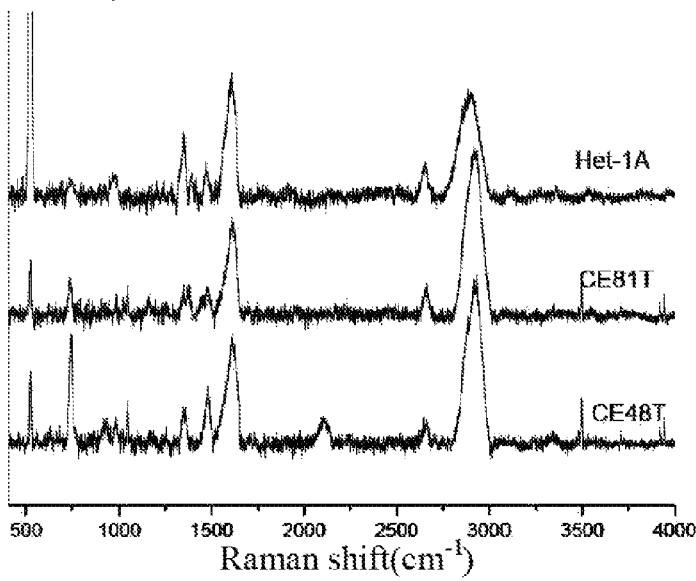
FIG. 7 illustrates a SERS spectrum of esophageal cancer cells and normal esophageal cancer cells measured with gold nanoparticles manufactured by sodium citrate reduction.
Figure 8:
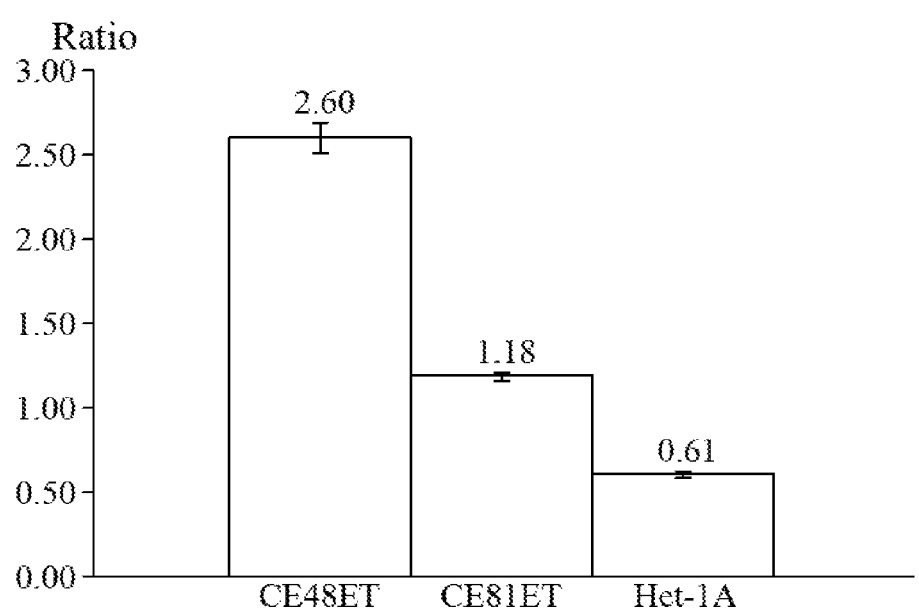
FIG. 8 illustrates bar graphs of signal intensities of valid signals in a first Raman peak and a second Raman peak of the spectrum in FIG. 7 fitted by a Gaussian function.

Raman spectra of the esophageal cancer cells and the normal esophageal cells, SERS spectra of the esophageal cancer cells and the normal esophageal cells, and analysis and comparison for the curve fitting of SERS spectra of the esophageal cancer cells and the normal esophageal cells The spectra of the esophageal cancer cells (CE48T and CE81T cells) and the normal esophageal cells (Het-1A) are shown in FIGS. 6 to 8. FIG. 6 illustrates a normal Raman spectrum of the esophageal cancer cells (CE48T and CE81T cells) and the normal esophageal cells (Het-1A), showing that the Raman signals of the cells are quite weak. FIG. 7 illustrates a SERS spectrum of esophageal cancer cells and normal esophageal cancer cells measured with gold nanoparticles manufactured by sodium citrate reduction. As shown in FIG. 7, when the cell is measured with gold nanoparticles manufactured by sodium citrate reduction, major SERS peaks are respectively at 735 cm$^{-1}$ (first Raman peak), 1342 cm$^{-1}$ (second Raman peak), 1450 cm$^{-1}$, and 1575 cm$^{-1}$. The SERS signal at the first Raman peak is apparent for esophageal cancer cells (CE48T and CE81T cells) but respectively weaker for the normal esophageal cells (Het-1A). Similarly, the SERS spectra in FIG. 7 are curved fitted with Gaussian function and presented in a form of ratio. The experiments are repeated three times, and the averaged value is provided in FIG. 8. As shown, the ratio between the signal intensity of the valid signal in the first Raman peak and the signal intensity of the valid signal in the second Raman peak of the CE48T cells and that between the CE81T cells are both greater than the ratio between the signal intensity of the valid signal in the first Raman peak and the signal intensity of the valid signal in the second Raman peak of the Het-1A cells (i.e., the normal cells). The fitting result for the esophageal cells is consistent with that for the oral cells.

As above, the instant disclosure uses metal nanoparticles as the substrate for measuring SERS signal of the cell sample, so that a cancer cell sample can be determined to be a cancer cell sample or a normal cell sample in a fast and accurate manner.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A cancer cell detection system, comprising:
   a sample holder holding a cell measurement component having a plurality of metal nanoparticles, and a cell sample being on the cell measurement component;
   a laser light source generating an incident light to illuminate the cell sample;
   a light detector detecting a surface enhanced Raman scattering signal of the cell sample; and
   a determine module coupled to the light detector and selectively determining if the cell sample comprises a cancer cell according to a signal intensity of a valid signal in a first Raman peak and a signal intensity of a valid signal in a second Raman peak of the surface enhanced Raman scattering signal;
   wherein, the first Raman peak is a signal position of a ring breathing mode of adenine, and the second Raman peak is a signal position of a stretching mode of adenine.

2. The cancer cell detection system according to claim 1, wherein the cell measurement component further comprises a base plate, and the metal nanoparticles are distributed over base plate.

3. The cancer cell detection system according to claim 1, wherein the determine module further calculates a ratio between the signal intensity of the valid signal in the first Raman peak and the signal intensity of the valid signal in the second Raman peak of the surface enhanced Raman scattering signal, and the cell sample is determined as the cancer cell sample when the ratio is greater than a threshold value.

4. The cancer cell detection system according to claim 3, wherein the threshold value is a ratio between a signal intensity of a valid signal in the first Raman peak and a signal intensity of a valid signal in the second Raman peak of a surface enhanced Raman scattering signal of normal cells.

5. The cancer cell detection system according to claim 1, wherein each of the signal intensities is a peak value of the corresponding valid signal.

6. The cancer cell detection system according to claim 1, wherein each of the signal intensities is a value of area integration of the corresponding valid signal.

7. The cancer cell detection system according to claim 1, wherein Raman peaks of two least valid signals among four strongest valid signals of adenine are respectively the signal position of the ring breathing mode of adenine and the signal position of the stretching mode of adenine.

8. The cancer cell detection system according to claim 1, wherein the stretching mode comprises a carbon-carbon stretching mode and a carbon-nitrogen stretching mode.

9. A detection method for cancer cell in vitro, comprising:
   utilizing a laser light source to illuminate a cell sample on a cell measurement component, wherein the cell measurement component comprises a plurality of metal nanoparticles;
   detecting a surface enhanced Raman scattering signal of the cell sample; and
   selectively determining if the cell sample comprises a cancer cell according to a signal intensity of a valid signal in a first Raman peak and a signal intensity of a valid signal in a second Raman peak of the surface enhanced Raman scattering signal;
   wherein, the first Raman peak is a signal position of a ring breathing mode of adenine, and the second Raman peak is a signal position of a stretching mode of adenine.

10. The detection method according to claim 9, further comprising utilizing a sample holder to hold and move the sample measurement component to an illumination region of the laser light source, prior to the illumination step.

11. The detection method according to claim 9, further comprising applying the cell sample on the cell measurement component, prior to the illumination step.

12. The detection method according to claim 9, wherein the cell measurement component further comprises a base plate, and the nanoparticles are distributed over the base plate.

13. The detection method according to claim 9, wherein the metal nanoparticles are a plurality of gold nanoparticles manufactured by sodium borohydride reduction.

14. The detection method according to claim 9, wherein the illumination step comprises utilizing the laser light source to generate an incident light having a wavelength of 632.8 nm to illuminate the cell sample.

15. The detection method according to claim 9, wherein the determination step further comprises calculating a ratio between the signal intensity of the valid signal in the first Raman peak and the signal intensity of the valid signal in the second Raman peak of the surface enhanced Raman scattering signal, and the cell sample is determined as the cancer cell sample when the ratio is greater than a threshold value.

16. The detection method according to claim 15, wherein the threshold value is a ratio between a signal intensity of a valid signal in the first Raman peak and a signal intensity of a valid signal in the second Raman peak of a surface enhanced Raman scattering signal of normal cells.

17. The detection method according to claim 9, wherein each of the signal intensities is a peak value of the corresponding valid signal.

18. The detection method according to claim 9, wherein each of the signal intensities is a value of area integration of the corresponding valid signal.

19. The detection method according to claim 9, wherein Raman peaks of two least valid signals among four strongest valid signals of adenine are respectively the signal position of the ring breathing mode of adenine and the signal position of the stretching mode of adenine.

20. The detection method according to claim 9, wherein the stretching mode comprises a carbon-carbon stretching mode and a carbon-nitrogen stretching mode.

* * * * *